United States Patent [19]

Nagano et al.

[11] Patent Number: 4,624,699
[45] Date of Patent: Nov. 25, 1986

[54] 2-SUBSTITUTED PHENYL-4,5,6,7-TETRAHYDRO-2H-INDAZOLES, THEIR PRODUCTION, AND USE AS HERBICIDES

[75] Inventors: Eiki Nagano, Hyogo; Ichiki Takemoto, Osaka; Masayuki Fukushima, Hyogo; Ryo Yoshida, Hyogo; Hiroshi Matsumoto, Hyogo, all of Japan

[73] Assignee: Sumitomo Chemical Company Limited, Osaka, Japan

[21] Appl. No.: 717,087

[22] Filed: Mar. 28, 1985

Related U.S. Application Data

[63] Continuation-in-part of Ser. No. 536,528, Sep. 28, 1983, abandoned.

[30] Foreign Application Priority Data

Sep. 28, 1982 [JP] Japan ................................ 57-170427
Nov. 6, 1982 [JP] Japan ................................ 57-194893
Mar. 16, 1983 [JP] Japan ................................ 58-045027

[51] Int. Cl.$^4$ ..................... A01N 43/56; C07D 231/56
[52] U.S. Cl. .......................................... 71/92; 548/369
[58] Field of Search ............................ 548/369; 71/92

[56] References Cited

U.S. PATENT DOCUMENTS 4,059,434 11/1977 Wolf .................................... 548/369

OTHER PUBLICATIONS

Morrison and Boyd, *Organic Chemistry*, 4th Edit., 1983, pp. 536 and 912.

*Primary Examiner*—Richard A. Schwartz
*Assistant Examiner*—Kurt G. Briscoe
*Attorney, Agent, or Firm*—Birch, Stewart, Kolasch & Birch

[57] ABSTRACT

A 2-substituted phenyl-4,5,6,7-tetrahydro-2H-indazole compound of the formula:

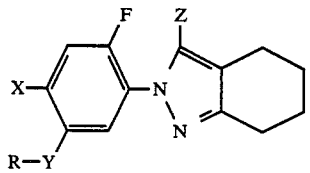

wherein X is a chlorine atom or a bromine atom, Y is an oxygen atom or an imino group, Z is a chlorine atom or a methyl group and R is a $C_1$–$C_6$ alkoxycarbonylmethyl group, a $C_3$–$C_6$ cycloalkoxycarbonylmethyl group or a $C_1$–$C_4$ haloalkoxycarbonylmethyl group, which is useful as a herbicide.

8 Claims, No Drawings

2-SUBSTITUTED PHENYL-4,5,6,7-TETRAHYDRO-2H-INDAZOLES, THEIR PRODUCTION, AND USE AS HERBICIDES

This is a continuation-in-part application of our application Ser. No. 536,528, filed Sept. 28, 1983 now abandoned.

The present invention relates to 2-substituted phenyl-4,5,6,7-tetrahydro-2H-indazoles (hereinafter referred to as "indazole(s)"), and their production and use.

The said indazoles are representable by the formula:

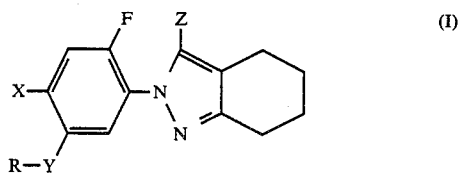

wherein X is a chlorine atom or a bromine atom, Y is an oxygen atom or an imino group, Z is chlorine atom or a methyl group and R is a $C_1$–$C_6$ alkoxycarbonylmethyl group, a $C_3$–$C_6$ cycloalkoxycarbonylmethyl group or a $C_1$–$C_4$ haloalkoxycarbonylmethyl group.

Preferred are the indazoles of the formula (I) wherein Z is a chlorine atom. The indazoles of the formula (I) wherein Y is an oxygen atom are also preferred. The indazoles of the formula (I) wherein Z is a chlorine atom and Y is an oxygen atom are particularly preferred.

It is known that certain kinds of indazoles are effective as herbicides. For instance, the herbicidal use of 3-chloro-2-(4-chloro-2-fluorophenyl)-4,5,6,7-tetrahydro-2H-indazole, 3-chloro-2-(2,4-dichloro-5-methoxyphenyl)-4,5,6,7-tetrahydro-2H-indazole, 3-methyl-2-(4-chloro-2-fluorophenyl)-4,5,6,7-tetrahydro-2H-indazole, etc. is disclosed in U.S. Pat. Nos. 4,059,434 and 4,124,374. However, their herbicidal effect is not necessarily satisfactory.

It has now been found that the indazoles (I) show a strong herbicidal activity against a wide variety of weeds including broad-leaved weeds and Graminaceous weeds in agricultural plowed fields as well as weeds in paddy fields at small doses and do not produce any material phytotoxicity on various agricultural crops (i.e. wheat, soybean, corn). Examples of broad-leaved weeds are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), radish (*Raphanus sativus*), wild mustard (*Brassica kaber*), hemp sesbania (*Sesbania exaltata*), velvetleaf (*Abutilon theophrasti*), prickly sida (*Sida spinosa*), cleavers (*Galium aparine*), ivyleaf morningglory (*Ipomoea hederacea*), tall morningglory (*Ipomoea purpurea*), field bindweed (*Convolvulus arvensis*), jimsonweed (*Datura stramonium*), black nightshade (*Solanum nigrum*), birdseye speedwell (*Veronica persica*), cocklebur (*Xanthium strumarium*), etc. Examples of Graminaceous weeds against which the indazoles (I) show a herbicidal activity are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oat (*Avena sativa*), wild oat (*Avena fatua*), Johnsongrass (*Sorghum halepense*), quackgrass (*Agropyron repens*), etc. Typical examples of the weeds which grow in paddy fields are barnyardgrass (*Echinochloa oryzicola*), monochoria (*Monochoria vaginalis*), arrowhead (*Sagittaria pygmaea*), false pimpernel (*Lindernia pyxidaria*), indian toothcup (*Rotala indica*), bulrush (*Scirpus juncoides*), slender spikerush (*Eleocharis acicularis*), long stemmed waterwort (*Elatine triandra*), etc.

The indazoles (I) are applicable either by soil treatment or foliar treatment, preferably by the latter, and their herbicidal effect is especially notable in crop fields such as fields of wheat, soybean or corn. Accordingly, the indazoles (I) can be used as herbicides applicable to agricultural plowed fields as well as paddy fields. They are also useful as herbicides to be employed for orchard, pasture land, lawn forest, non-agricultural field, etc. applications.

The indazole (I) is obtainable by reacting a 2,4-dihalo-5-substituted phenyl-4,5,6,7-tetrahydro-2H-indazole of the formula:

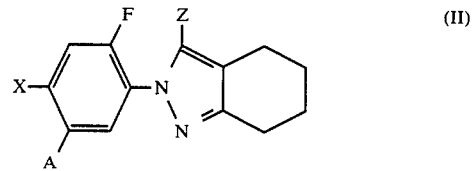

wherein x and z are each as defined above and A is an amino group or a hydroxyl group with a halogenated compound of the formula:

wherein R is as defined above and B is a halogen atom.

The reaction is usually carried out in a solvent in the presence or absence of a base at a temperature of from −80° to 200° C. for a period of 0.5 to 20 hours. The halogenated compound (III) is normally employed in an amount of 1 to 3 equivalents with respect to the starting compound (II). The amount of the base may be ordinarily from 1 to 2 equivalents with respect to the starting compound (II). Examples of the solvent are aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), acid amides (e.g. dimethylformamide, dimethylacetamide), water, or their mixtures. As the base, there may be exemplified organic bases (e.g. pyridine, triethylamine, N,N-diethylaniline), inorganic bases (e.g. sodium hydride, sodium hydroxide, potassium hydroxide, sodium carbonate, potassium carbonate), etc.

The thus produced indazole (I) may be subjected to ordinary post-treatment and, when desired, purified by a per se conventional procedure such as column chromatography or recrystallization.

Practical and presently preferred embodiments of the production of the objective indazoles (I) are illustratively shown below:

EXAMPLE 1

Into a solution of 3-chloro-2-(4-chloro-2-fluoro-5-hydroxyphenyl)-4,5,6,7-tetrahydro-2H-indazole (30 mg) in dimethylformamide (1 ml), there were added potassium carbonate (10 mg) and ethyl bromoacetate (20 mg), and the mixture was stirred at 80° C. for 3 hours. After cooling, water was added to the reaction mixture, followed by extraction with ether. The ether layer was washed with water twice, dried and concentrated. The residue was purified by thin layer chromatography to give 1.8 mg of 3-chloro-2-(4-chloro-2-fluoro-5-ethoxycarbonylmethoxyphenyl-4,5,6,7-tetrahydro-2H-indazole (Compound No. 1) as a glassy substance.

MS (m/e): 390, 388, 386, 351, 313.

IR$\nu_{max}$ (cm$^{-1}$): 1750.

Examples of the indazole (I) produced in the same manner as above are shown in Table 1.

TABLE 1

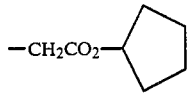

| Compound No. | X | Y | Z | R | Physical property |
|---|---|---|---|---|---|
| 1 | Cl | O | Cl | —CH$_2$CO$_2$C$_2$H$_5$ | glassy |
| 2 | Cl | O | Cl | —CH$_2$COC$_5$H$_{11}$(n) | m.p. 74–75° C. |
| 3 | Cl | O | Cl | —CH$_2$CO$_2$CH$_2$CH$_2$Cl | m.p. 96–97° C. |
| 4 | Cl | O | Cl | —CH$_2$CO$_2$CH$_2$CH$_2$Br | m.p. 121–122° C. |
| 5 | Cl | O | Cl | —CH$_2$CO$_2$—⬠ | m.p. 97–98° C. |
| 6 | Cl | O | CH$_3$ | —CH$_2$CO$_2$C$_2$H$_5$ | n$_D^{24}$ 1.5374 |
| 7 | Cl | O | CH$_3$ | —CH$_2$CO$_2$C$_5$H$_{11}$(n) | m.p. 78–79° C. |
| 8 | Cl | —NH | CH$_3$ | —CH$_2$CO$_2$C$_2$H$_5$ | m.p. 126–128° C. |
| 9 | Cl | —NH | CH$_3$ | —CH$_2$CO$_2$C$_5$H$_{11}$(n) | m.p. 124–125.5° C. |
| 10 | Br | —NH | CH$_3$ | —CH$_2$CO$_2$CH$_3$ | glassy |

The starting 2,4-dihalo-5-substituted phenyl-4,5,6,7-tetrahydro-2H-indazole (II) wherein A is a hydroxyl group and Z is a chlorine atom is obtainable by reacting a 2,4-dihalo-5-hydroxyphenylhydrazine of the formula:

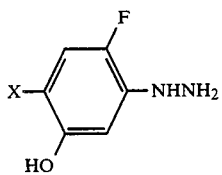

wherein X is as defined above with the 2-alkoxycarbonylcyclohexanone of the formula:

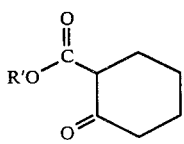

wherein R' is a C$_1$–C$_4$ alkyl group to give a 2-(2,4-dihalo-5-hydroxyphenyl)hexahydroindazol-3-one of the formula:

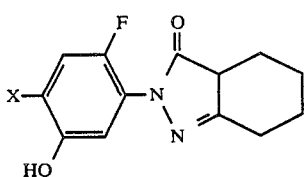

wherein X is as defined above, followed by reacting the latter with a chlorinating agent.

The first reaction may be carried out in a solvent at a temperature of 80° to 200° C. for a period of 0.5 to 20 hours. The 2-alkoxycarbonylcyclohexanone (V) is usually employed in an amount of 1 to 1.2 equivalents with respect to the 2,4-dihalo-5-hydroxyphenylhydrazine (IV). Examples of the solvent are toluene, xylene, acetic acid, etc.

The second reaction is normally carried out in a solvent at a temperature of 80° for 200° C. for a period of 5 to 20 hours. The chlorinating agent may be employed in an excessive amount with respect to the intermediary product (VI). Examples of the chlorinating agent are phosphorus oxychloride, thionyl chloride, phosgene, oxalic dichloride, trichloromethyl chloroformate, etc. Examples of the solvent are toluene, xylene, chloroform, etc.

The 2,4-dihalo-5-substituted phenyl-4,5,6,7-tetrahydro-2H-indazole (II) wherein A is a hydroxyl group and Z is a methyl group may be also produced by reacting the 2,4-dihalo-5-hydroxyphenylhydrazine (IV) with 2-acetylcyclohexanone.

The reaction may be carried out in a solvent in the presence of an acid catalyst at a temperature of 80° to 200° C. for a period of 0.5 to 20 hours. The 2-acetylcyclohexanone is usually employed in an amount of 1 to 1.2 equivalents with respect to the 2,4-dihalo-5-hydroxyphenylhydrazine (IV). As the solvent, there may be employed preferably aromatic hydrocarbons such as toluene, xylene, α-methylnaphthalene, or a mixture thereof. Examples of the acid catalyst are inorganic acids (e.g. hydrochloric acid, sulfuric acid), organic acids (e.g. acetic acid, p-toluenesulfonic acid), etc.

The 2,4-dihalo-5-substituted phenyl-4,5,6,7-tetrahydro-2H-indazole (II) wherein A is an amino group is obtainable by reacting a 2,4-dihalo-5-nitrophenylhydrazine of the formula:

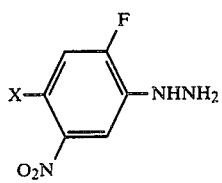

wherein X is as defined above with the 2-alkoxycarbonylcyclohexanone (V) as in the reaction between the compound (IV) and the compound (V) to give a 2-(2,4-dihalo-5-nitrophenyl)hexahydroindazol-3-one of the formula:

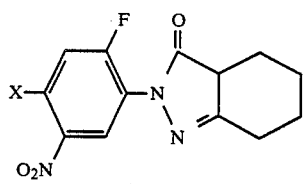

(VIII)

wherein X is as defined above, followed by reacting the latter with a chlorinating agent as in the reaction between the compound (VI) and the chlorinating agent, or by reacting the 2,4-dihalo-5-nitrophenylhydrazine (VII) with 2-acetylcyclohexanone as in the reaction between the compound (IV) and 2-acetylcyclohexanone to give a 2,4-dihalo-5-nitrophenyl-4,5,6,7-tetrahydro-2H-indazole of the formula:

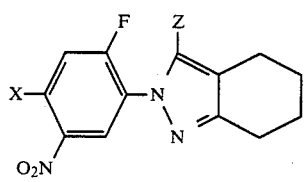

(IX)

wherein X and Z are as defined above, followed by subjecting the latter to reduction by a per se conventional procedure such as reduction with an acid (e.g. hydrochloric acid, acetic acid) and iron powder.

The intermediary phenylhydrazine compounds, i.e. the 2,4-dihalo-5-hydroxyphenylhydrazine (IV) and the 2,4-dihalo-5-nitrophenylhydrazine (VII), may be produced according to the following scheme:

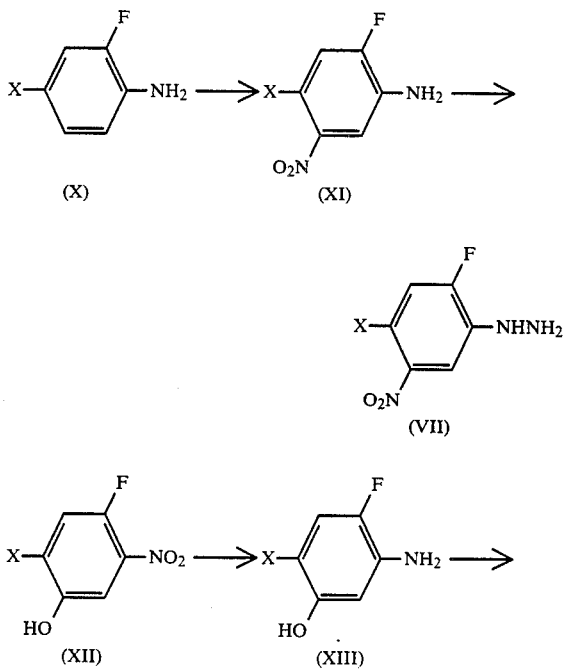

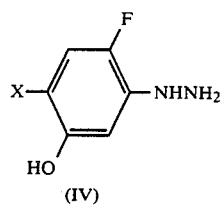

(IV)

wherein X is as defined above.

The above conversions are known and described, for instance, in U.S. Pat. No. 4,124,374, EP-0061741A, EP-0083055A and J.Chem.Soc., Commun., 2106 (1970).

Typical examples for the production of the starting compounds are illustratively shown below:

EXAMPLE 2

Production of the 2,4-dihalo-5-substituted phenyl-4,5,6,7-tetrahydro-2H-indazole (II: X=Z=Cl; A=OH):

A solution of 2-fluoro-4-chloro-5-hydroxyphenylhydrazine (8 g) and 2-ethoxycarbonylcyclohexanone (8 g) in acetic acid (30 ml) was heated under reflux for 4 hours. After cooling, the precipitated crystals were collected by filtration and washed with ether to give 11 g of 2-(4-chloro-2-fluoro-5-hydroxyphenyl)-2,3a,4,5,6,7-hexahydroindazol-3-one. m.p. 273°–275° C. (decomp.).

The product thus obtained was added to a 1M solution of phosgene in toluene (400 ml), and the resultant mixture was heated under reflux for 3 hours. After cooling, the mixture was concentrated, and the residue was purified by silica gel column chromatography to obtain 3 g of 3-chloro-2-(4-chloro-2-fluoro-5-hydroxyphenyl)-4,5,6,7-tetrahydro-2H-indazole. m.p., 183°–185° C.

Example 3

Production of the 2,4-dihalo-5-substituted phenyl-4,5,6,7-tetrahydro-2H-indazole (II: X=Br; Z=Cl; A=OH):

In the same manner as in Example 2 but using 4-bromo-2-fluoro-5-hydroxyphenylhydrazine, there was obtained 3-chloro-2-(4-bromo-2-fluoro-5-hydroxyphenyl)-4,5,6,7-tetrahydro-2H-indazole. m.p., 174.3° C.

EXAMPLE 4

Production of the 2,4-dihalo-5-substituted phenyl-4,5,6,7-tetrahydro-2H-indazole (II: X=Cl, Z=CH$_3$; A=OH):

4-Chloro-2-fluoro-5-hydroxyphenylhydrazine (0.5 g), 2-acetylcyclohexanone (0.4 g) and a catalytic amount of acetic acid were admixed with xylene (15 ml), and the resultant mixture was heated under reflux for 5 hours while removing water. After cooling, the mixture was concentrated, and the residue was purified by silica gel column chromatography to obtain 0.7 g of 2-(4-chloro-2-fluoro-5-hydroxyphenyl)-3-methyl-4,5,6,7-tetrahydro-2H-indazole.
m.p. 188.5°–190° C.

EXAMPLE 5

Production of the 2,4-dihalo-5-substituted phenyl-4,5,6,7-tetrahydro-2H-indazole (II: X=Cl; Z=CH$_3$; A=NH$_2$):

A mixture of iron powder (3 g) and a 5% aqueous acetic acid solution (10 ml) was heated at 90° to 100° C.

while stirring for 10 minutes. To the resulting mixture, there was dropwise added 2-(4-chloro-2-fluoro-5-nitrophenyl)-3-methyl-4,5,6,7-tetrahydro-2H-indazole (2 g) in acetic acid (10 ml) and ethyl acetate (10 ml), followed by stirring at the same temperature for 1 hour. After cooling, the iron powder was eliminated by filtration, and the filtrate was extracted with ethyl acetate. The organic layer was washed with a saturated sodium bicarbonate solution, dried and concentrated. The crystallized residue was collected by filtration and washed with ether to obtain 1.8 g of 2-(4-chloro-2-fluoro-5-aminophenyl)-3-methyl-4,5,6,7-tetrahydro-2H-indazole, m.p., 107°–108° C.

Some examples of the 2,4-dihalo-5-substituted phenyl-4,5,6,7-tetrahydro-2H-indazole (II) wherein A is an amino group produced in the same manner as in Example 5 are shown in Table 2.

TABLE 2

(II)

| X | Z | Physical property |
|---|---|---|
| Br | Cl | glassy |
| Br | $CH_3$ | m.p. 69–71° C. |

EXAMPLE 6

Production of the substituted phenylhydrazine (IV):

4-Chloro-2-fluoro-5-hydroxyaniline (10 g) was dissolved in conc. hydrochloric acid (130 ml) under heating, and the resultant mixture was cooled to 0° C. To the resulting mixture, there was dropwise added a solution of sodium nitrite (4.5 g) in water (20 ml). After completion of the addition, the mixture was further stirred at 5 to −5° C. for 1 hour, and urea was added thereto, whereby excessive sodium nitrite ion was decomposed. The resulting mixture was cooled to −30° to −25° C., and a solution of anhydrous stannous chloride (20.5 g) in conc. hydrochloric acid (40 ml) was added thereto, followed by stirring at −10° to 0° C. for 3 hours. The precipitated crystals were collected by filtration, washed with a small amount of water and dissolved in a 10% aqueous sodium hydroxide solution. The resultant solution was adjusted to pH 7 and extracted with ethyl acetate. The extract was dried and concentrated. The crystallized residue was washed with ether to obtain 1 g of 4-chloro-2-fluoro-5-hydroxyphenylhydrazine. m.p., 149°–150° C. (decomp.).

Some examples of the substituted phenylhydrazines (VII) produced in the same manner as in Example 6 are shown in Table 3.

TABLE 3

(VII)

| X | Physical property |
|---|---|
| Cl | m.p. 116–117° C. |

TABLE 3-continued (VII)

| X | Physical property |
|---|---|
| Br | m.p. 110–111° C. |

EXAMPLE 7

Production of the 2,4-dihalo-5-nitrophenyl-4,5,6,7-tetrahydro-2H-indazole (IX):

In the same manner as in Example 4 but using 4-chloro-2-fluoro-5-nitrophenylhydrazine (4 g), 2-acetylcyclohexanone (2.8 g), a catalytic amount of acetic acid and xylene (10 ml), there was produced 2.3 g of 2-(4-chloro-2-fluoro-5-nitrophenyl)-3-methyl-4,5,6,7-tetrahydro-2H-indazole. m.p., 143°–144° C.

EXAMPLE 8

Production of the 2,4-dihalo-5-nitrophenyl-4,5,6,7-tetrahydro-2H-indazole (IX):

In the same manner as in Example 2 but using a solution of 4-chloro-2-fluoro-5-nitrophenylhydrazine (4.6 g), and 2-ethoxycarbonylcyclohexanone (3.9 g) in acetic acid (20 ml), there was prepared 2-(4-chloro-2-fluoro-5-nitrophenyl)-2,3a,4,5,6,7-hexahydroindazol-3-one (4.2 g).

The thus obtained product was treated with a 1M solution of phosgene in toluene (300 ml) in the same manner as in Example 5 to obtain 0.8 g of 3-chloro-2-(4-chloro-2-fluoro-5-nitrophenyl)-4,5,6,7-tetrahydro-2H-indazole. m.p., 120°–122° C.

EXAMPLE 9

Production of the nitroaniline (XI):

4-Chloro-2-fluoroaniline (23 g) was dissolved in conc. sulfuric acid (120 ml), and the resultant mixture was cooled to −20° C., followed by dropwise addition of fuming nitric acid (15 g). The reaction mixture was stirred at −20° to −15° C. for 1.5 hours, poured into ice-water and then extracted with ether. The ether extract was washed with water and a saturated sodium bicarbonate solution, dried and concentrated. The residue was crystallized from a mixture of toluene and hexane (2:1) to obtain 20 g of 4-chloro-2-fluoro-5-nitroaniline. m.p., 83°–84.5° C.

EXAMPLE 10

In the same manner as in Example 9 but using 4-bromo-2-fluoroaniline, there was obtained 4-bromo-2-fluoro-5-nitroaniline. m.p., 90°–92° C.

In the practical usage of the indazoles (I), they may be applied in any preparation form such as emulsifiable concentrates, wettable powders, suspensions, granules, etc. in combination with a conventional solid or liquid carrier or diluent, a surface active agent or an auxiliary agent.

The content of the indazole (I) as the active ingredient in such preparation form is usually within a range of 0.03 to 80% by weight, preferably of 0.07 to 70% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to those shown in Table 1.

PREPARATION EXAMPLE 1

Fifty parts of Compound No. 2, 3 parts of calcium ligninsulfonate, 2 parts of sodium laurylsulfate and 45 parts of synthetic hydrous silicate are well mixed while being powdered to obtain a wettable powder.

PREPARATION EXAMPLE 2

Ten parts of Compound No. 6, 14 parts of polyoxyethylenestyrylphenyl ether, 6 parts of calcium dodecylbenzenesulfonate and 70 parts of cyclohexanone are well mixed while being powdered to obtain an emulsifiable concentrate.

PREPARATION EXAMPLE 3

Two parts of Compound No. 3, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

PREPARATION EXAMPLE 4

Twenty-five parts of Compound No. 2 is mixed with 3 parts of polyoxyethylene sorbitan monooleate, 3 parts of carboxymethyl cellulose and 69 parts of water and pulverized until the particle size of the active ingredient becomes less than 5 microns to obtain a suspension.

The indazoles (I) thus formulated in any suitable preparation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the indazoles (I) over the top of the plants. It may also be applied directly to the weeds if care is taken to keep the chemical off the crop foliage.

The indazoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

The dosage rate of the indazoles (I) may vary depending on prevailing weather conditions, preparation used, prevailing season, mode of application, soil involved, crop and weed species, etc. Generally, however, the dosage rate is from 0.01 to 40 grams, preferably from 0.05 to 30 grams, of the active ingredient per are. The herbicidal composition of the invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological data of the indazoles (I) as herbicides will be illustratively shown in the following Examples wherein the phytotoxicity to crop plants and the herbicidal activity on weeds were obtained visually as to the degree of germination as well as the growth inhibition and rated with an index 0, 1, 2, 3, 4 or 5, in which the numeral "0" indicates that no material difference is seen in comparison with the untreated plant and the numeral "5" indicates the complete inhibition or death of the test plants.

The compounds shown in Table 4 below were used for comparison.

TABLE 4

| Compound No. | Chemical structures | Remarks |
|---|---|---|
| A | 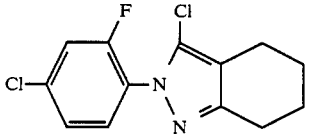 | U.S. Pat. No. 4,059,434 |
| B | 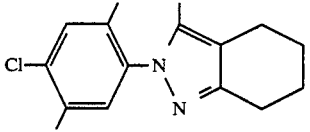 | U.S. Pat. No. 4,059,434 |
| C | 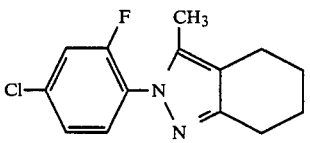 | U.S. Pat. No. 4,124,374 |
| D | 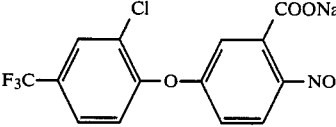 | Commercially available herbicide; "aciflurorufen" |

TEST EXAMPLE 1

Plastic pots (diameter, 10 cm; height, 10 cm) were filled with upland field soil, and the seeds of Japanese millet, redroot pigweed and velvetleaf were sowed in the pots, and the soil was covered thereover. A designed amount of the test compound formulated into an emulsifiable concentrate according to Preparation Example 2 and diluted with water was sprayed over the top to the soil surface at a spray volume of 10 liters per are by means of a small hand sprayer, and the soil was well mixed at the depth of 4 cm. Thereafter, the test plants were cultivated in a greenhouse for 20 days and the herbicidal activity was examined. The results are shown in Table 5.

TABLE 5

| Compound No. | Dosage (g/are) | Herbicidal activity |||
|---|---|---|---|---|
| | | Japanese millet | Redroot pigweed | Velvetleaf |
| 1 | 20 | 5 | 5 | 5 |
|   | 5  | — | 5 | 5 |
| 2 | 20 | 4 | 5 | 5 |
|   | 5  | — | 5 | 5 |
| 3 | 20 | 5 | 5 | 5 |
|   | 5  | — | 5 | 5 |
| 4 | 20 | 4 | 5 | 5 |
|   | 5  | 3 | 5 | 5 |
| 5 | 20 | 4 | 5 | 5 |
|   | 5  | 3 | 5 | 5 |
| 6 | 20 | 4 | 5 | 5 |
|   | 5  | — | 5 | 5 |
| 7 | 20 | — | 5 | 5 |
|   | 5  | — | 5 | 5 |
| 8 | 20 | 3 | 5 | 5 |
|   | 5  | — | 5 | 4 |
| 9 | 20 | 3 | 5 | 5 |
|   | 5  | — | 5 | 4 |
| 10| 20 | 3 | 5 | 5 |
|   | 5  | — | — | 4 |
| C | 80 | 4 | 5 | 5 |
|   | 20 | 3 | 3 | 3 |

TEST EXAMPLE 2

Vats (33 cm×23 cm×11 cm) were filled with upland field soil and the seeds of corn, wheat, soybean, hemp sesbania, cocklebur, velvetleaf, tall morningglory, redroot pigweed, black nightshade and prickly sida were sowed therein. Cultivation was carried out in a greenhouse for 18 days. A designed amount of the test compound formulated into an emulsifiable concentrate according to Preparation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity and the phytotoxicity were examined. At the time of the application, the growing stage of the test plants varied depending on their species but, they were generally at the 1 to 4 leaf stage and at a height of 2 to 12 cm. The results are shown in Table 6.

TABLE 6

| Compound No. | Dosage (g/are) | Phytotoxicity ||| Herbicidal activity |||||||
|---|---|---|---|---|---|---|---|---|---|---|---|
| | | Corn | Wheat | Soybean | Hemp sesbania | Cocklebur | Velvetleaf | Tall morningglory | Redroot pigweed | Black nightshade | Prickly sida |
| 2 | 2.5  | — | 1 | — | 5 | 5 | 5 | 5 | 5 | 5 | 5 |
|   | 0.63 | 1 | 1 | 1 | 5 | 5 | 5 | 4 | 5 | 5 | 5 |
|   | 0.16 | 0 | 0 | 1 | 5 | 4 | 5 | 4 | 5 | 5 | 4 |
| 3 | 2.5  | — | 1 | — | 5 | 5 | 5 | 5 | 5 | 5 | 5 |
|   | 0.63 | 1 | 1 | 1 | 5 | 5 | 5 | 5 | 5 | 5 | 5 |
|   | 0.16 | 0 | 0 | 1 | 5 | 4 | 5 | 4 | 5 | 5 | 4 |
| 6 | 2.5  | — | 0 | 0 | 4 | 4 | 5 | 5 | 5 | 5 | 5 |
|   | 0.63 | 0 | 0 | 0 | 4 | 3 | 5 | 4 | 5 | 5 | 4 |
|   | 0.16 | 0 | 0 | 0 | 3 | — | 5 | 4 | 5 | 5 | — |
| 7 | 2.5  | — | 1 | 1 | 5 | 5 | 5 | 5 | 5 | 5 | 5 |
|   | 0.63 | 1 | 0 | 0 | 5 | 5 | 5 | 4 | 5 | 5 | 5 |
|   | 0.16 | 0 | 0 | 0 | 4 | 4 | 5 | 4 | 5 | 5 | 3 |
| 9 | 0.63 | 1 | 0 | 1 | 5 | 4 | 5 | 5 | 5 | 5 | 4 |
|   | 0.16 | 1 | 0 | 0 | 5 | 3 | 5 | 5 | 5 | 5 | 3 |
| A | 0.32 | 1 | 0 | 3 | 4 | 3 | 4 | 2 | 1 | 3 | — |
|   | 0.16 | 1 | 0 | 2 | 2 | 2 | 3 | 0 | 1 | 2 | — |
|   | 0.08 | 0 | 0 | 1 | 1 | 1 | 1 | 0 | 0 | 1 | — |
| B | 0.63 | 1 | 0 | 3 | 4 | 3 | 4 | 2 | 2 | 3 | 3 |
|   | 0.16 | 1 | 0 | 2 | 2 | 1 | 3 | 0 | 1 | 2 | 1 |
| C | 5.0  | 2 | 2 | 3 | 4 | 4 | 5 | 5 | 5 | — | 3 |
|   | 1.25 | 1 | 1 | 3 | 3 | 3 | 5 | 2 | 5 | — | 0 |
|   | 0.32 | 1 | 1 | 3 | 2 | 1 | 3 | 1 | 3 | — | 0 |
| D | 1.25 | 1 | 1 | 2 | 5 | 3 | 3 | 4 | 5 | 4 | — |
|   | 0.32 | 0 | 0 | 1 | 3 | 1 | 1 | 2 | 3 | 2 | — |

TEST EXAMPLE 3

Seeds of corn, cocklebur, velvetleaf, field bindweed and prickly sida were sowed in the field as previously laid up in ridges, each ridge having an upper width of 1 m and being plotted in 3 m². When soybean grew to the 1.2-leaf stage, a designed amount of the test compound formulated into an emulsifiable concentrate according to Preparation Example 2 was dispersed in water containing a spreading agent and sprayed to the foliage of the test plants by means of a small hand sprayer at a spray volume of 5 liters per are. The application was made with three replications. At the time of the application, the test plants were generally in 1 to 4-leaf stages, while they varied depending on the species. After cultivation for 21 days, the herbicidal activity on the weeds as well as the phytotoxicity on soybean were evaluated as follows: the aerial parts of the test plants were cut off and weighed (fresh weight); the percentage of the fresh weight of the treated plant to that of the untreated plant was calculated with the latter fresh weight taken as 100;

and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and control weeds, respectively.

| Rating value | Fresh weight (percentage to untreated plot) (%) | |
|---|---|---|
| | Weeds | Soybean |
| 0 | 91– | 91– |
| 1 | 71–90 | 71–90 |
| 2 | 41–70 | 51–70 |
| 3 | 11–40 | 31–50 |
| 4 | 4–10 | 11–30 |
| 5 | 0–3 | 0–10 |

The results are shown in Table 7.

TABLE 7

| Compound No. | Dosage (g/are) | Phytotoxicity Soybean | Herbicidal activity | | | |
|---|---|---|---|---|---|---|
| | | | Cocklebur | Velvetleaf | Field bindweed | Prickly sida |
| 2 | 1 | 1 | 4 | 5 | 4 | 4 |
| | 0.5 | 0 | 3 | 4 | 3 | 4 |
| D | 1 | 0 | 2 | 1 | 2 | 0 |
| | 0.5 | 0 | 1 | 0 | 1 | 0 |

What is claimed is:

1. A 2-substituted phenyl-4,5,6,7-tetrahydro-2H-indazole compound of the formula:

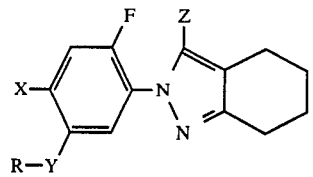

wherein X is a chlorine atom or a bromine atom, Y is an oxygen atom or an imino group, Z is a chlorine atom or a methyl group and R is a $C_1$–$C_6$ alkoxycarbonylmethyl group, a $C_3$–$C_6$ cycloalkoxycarbonylmethyl group or a $C_1$–$C_4$ haloalkoxycarbonylmethyl group.

2. The compound according to claim 1, wherein Z is a chlorine atom.

3. The compound according to claim 1, wherein Y is an oxygen atom.

4. The compound according to claim 1, wherein Z is a chlorine atom and Y is an oxygen atom.

5. The compound 3-chloro-2-(2-fluoro-4-chloro-5-n-pentyloxycarbonylmethoxyphenyl)-4,5,6,7-tetrahydro-2H-indazole.

6. A herbicidal composition which comprises as an active ingredient a herbicidally effective amount of the compound according to claim 1, and an inert carrier or diluent.

7. A method for controlling weeds which comprises applying a herbicidally effective amount of the compound according to claim 1 to the area where weeds grow or will grow.

8. A method for controlling weeds which comprises applying a herbicidally effective amount of the compound according to claim 1 to the area where soybean is or will be cultivated.

* * * * *